US011865010B2

(12) United States Patent
Landon (10) Patent No.: US 11,865,010 B2
(45) Date of Patent: Jan. 9, 2024

(54) COMPLIANT ANTI-RESORPTION IMPLANT

(71) Applicant: Smith & Nephew, Inc., Memphis, TN (US)

(72) Inventor: Ryan L. Landon, Southaven, MS (US)

(73) Assignee: SMITH & NEPHEW, INC., Memphis, TN (US)

( * ) Notice: Subject to any disclaimer, the term of this patent is extended or adjusted under 35 U.S.C. 154(b) by 397 days.

(21) Appl. No.: 16/219,534

(22) Filed: Dec. 13, 2018

(65) Prior Publication Data

US 2019/0110898 A1   Apr. 18, 2019

Related U.S. Application Data

(63) Continuation of application No. 14/368,341, filed as application No. PCT/US2013/020468 on Jan. 7, 2013, now Pat. No. 10,226,347.

(60) Provisional application No. 61/587,854, filed on Jan. 18, 2012.

(51) Int. Cl.
*A61F 2/38* (2006.01)
*A61F 2/30* (2006.01)

(52) U.S. Cl.
CPC .......... *A61F 2/3859* (2013.01); *A61F 2/3094* (2013.01); *A61F 2002/30006* (2013.01); *A61F 2002/30011* (2013.01); *A61F 2002/30014* (2013.01); *A61F 2002/3082* (2013.01); *A61F 2002/30879* (2013.01); *A61F 2002/30971* (2013.01); *A61F 2002/30985* (2013.01)

(58) Field of Classification Search
CPC .................. A61F 2/3859; A61F 2/3094; A61F 2002/30006; A61F 2002/30011; A61F 2002/30014
See application file for complete search history.

(56) References Cited

U.S. PATENT DOCUMENTS

| | | | |
|---|---|---|---|
| 3,837,009 | A | 9/1974 | Walker |
| 4,908,033 | A | 3/1990 | Frey et al. |
| 5,549,684 | A | 8/1996 | Amino et al. |
| 5,725,584 | A | 3/1998 | Walker et al. |
| 8,070,821 | B2 | 12/2011 | Roger |

(Continued)

FOREIGN PATENT DOCUMENTS

GB      2162425 A      2/1986

OTHER PUBLICATIONS

Examination Report sections 12 & 13 of the Patents Act for Indian Patent Application No. 5996/DELNP/2014, dated Dec. 6, 2019.

(Continued)

*Primary Examiner* — Jerrah Edwards
*Assistant Examiner* — Christine L Nelson
(74) *Attorney, Agent, or Firm* — KDW Firm PLLC (57) ABSTRACT

Systems, devices, and methods are described for providing orthopedic implants that reduces the negative effects of stress shielding on surrounding bone structure. The orthopedic implants are comprised of two portions, a shell portion that forms an articulation interfaces and an intermediate portion that forms a bone interface. The shell portion is designed to reduce absorption of Carticulation forces and evenly distribute incident forces to the intermediate portion. The intermediate portion is designed to form a strong interface with native bone and transmit forces from the shell into the bone.

20 Claims, 9 Drawing Sheets

(56) References Cited

U.S. PATENT DOCUMENTS

| | | | |
|---|---|---|---|
| 8,333,805 B2 | 12/2012 | Williams, III et al. | |
| 2002/0065562 A1 | 5/2002 | Storer et al. | |
| 2006/0178749 A1 | 8/2006 | Pendleton et al. | |
| 2007/0233266 A1* | 10/2007 | Williams, III | A61F 2/36 623/20.14 |
| 2007/0276399 A1 | 11/2007 | Medley et al. | |
| 2008/0288083 A1 | 11/2008 | Axelsson et al. | |
| 2009/0210068 A1 | 8/2009 | Zeller et al. | |
| 2010/0256758 A1 | 10/2010 | Gordon et al. | |
| 2010/0268337 A1 | 10/2010 | Gordon et al. | |
| 2012/0010617 A1* | 1/2012 | Ramos Maza | A61B 17/8052 606/281 |

OTHER PUBLICATIONS

European Patent Office, First Office Action, dated Nov. 4, 2016, 5 pages.
Australian Patent Office, Patent Examination Report No. 1, dated Sep. 29, 2016, 4 pages.
Chinese Patent Office, Second Office Action, dated Jun. 1, 2016, 15 pages including English translation.
European Patent Office, European Search Report, dated Jul. 8, 2015, 6 pages.
Chinese Patent Office, First Office Action with translation, dated Aug. 18, 2015, 18 pages.
International Search Report dated Apr. 18, 2013 for PCT/US2013/020468.

\* cited by examiner

COMPLIANT ANTI-RESORPTION IMPLANT

CROSS-REFERENCE TO RELATED APPLICATION

This application is a continuation of U.S. patent application Ser. No. 14/368,341, filed Jun. 24, 2014, now U.S. Pat. No. 10,226,347, entitled "Compliant Anti-Resorption Implant", which is a United States National Stage filing under 35 U.S.C. § 371 of International Application No. PCT/US2013/020468, filed Jan. 7, 2013, which claims the benefit of U.S. Provisional Application No. 61/587,854, filed Jan. 18, 2012, each of which is hereby incorporated by reference herein in its entirety. International Application No. PCT/US2013/020468 was published under PCT Article 21(2) in English.

BACKGROUND

Orthopedic implants are used to strengthen or replace joints that typically experience high levels of stress and wear. In a primary replacement surgery, joints that have experienced trauma or have been worn to a degree that inhibits normal functioning of the joint are replaced or reinforced with stronger wear-resistant implants. In a revision surgery, primary implants that have either been unsuccessful or have worn to a degree that inhibits their function are supplemented or replaced with revision implants. The constant daily stress and wear at the replacement joints, especially for weight-bearing knee replacements, require both primary and revision implants to be strong enough to withstand significant abuse.

Conventional knee implants are made of rigid, high-modulus metals used to provide ample support and to withstand the high stresses typically present at the knee joint. High-strength metals such as titanium, stainless steel, zirconium, cobalt-chrome alloy, and other metal alloys are often used in femoral and tibial implants to achieve the strength and stability required. These metal components exhibit higher rigidity and higher modulii of elasticity than the bone structure into which they are implanted in order to withstand the significant stresses that are incident on the knee joint during everyday activity. The size of the implants and the metal materials used to make them results in a heavy implanted component that a patient must adjust to, and patients may experience discomfort from "feeling the weight" of the metal component after implantation.

With the rigid materials and the large implant designs of traditional knee implant components, the knee replacements bear a majority of stresses incident on a patient's joint after implantation. As a result, the bone surrounding the implant often experiences lower stresses than normal. The decreased stresses cause bone resorption as the bone breaks down to adjust and accommodate the decreased need for support from the bone at the joint. In response to the changes in normal loading, a bone remodels itself to either build up more mass to strengthen the bone or break down bone mass to weaken the bone. This process is known as Wolff's law, and it causes a normal bone to become stronger if loading on the bone increases or weaker if loading on the bone decreases.

Bone resorption around an implant can have significant negative effects, as it decreases the integrity of the bone and its ability to hold the implant solidly in place. This complication is known as stress shielding as the high-strength implant "shields" the surrounding bone from stress and loading that is necessary to cause the bone to maintain its strength. The resulting bone resorption causes patients to experience pain and feel the weight of their knee implants during their everyday activities. In some cases, the bone resorption resulting from stress shielding can even cause an implant to fail completely, necessitating a second revision knee replacement surgery.

SUMMARY

Disclosed herein are systems, devices, and methods for providing an orthopedic implant that reduces the negative effects of stress shielding on surrounding bone structure. In particular, the systems, devices, and methods provide orthopedic implants that transmit forces incident on the implant to surrounding bone structure. The systems, devices, and methods reduce points of device stress concentration and provide uniform distribution of the stress transmitted to the surrounding bone.

In certain embodiments, an orthopedic implant includes a shell region having an outer articulation surface and an intermediate region having a bone interface and different mechanical properties than the shell region. In certain implementations, the intermediate region has a different modulus of elasticity, density, or porosity than the shell region. In certain implementations, the intermediate region is comprised of a different material than the shell region.

In certain implementations, the shell region includes strengthening ribs. The strengthening ribs may be disposed at an anterior portion of the shell, on condylar portions of the shell, at a junction between condylar portions of the shell, or a combination thereof. The ribs may be disposed on a surface of the shell region, or may be disposed in an internal portion of the shell region.

In certain implementations, the cross-sectional area of the shell region is substantially uniform. In such implementations, the thickness of the shell region is varied throughout the shell. In other implementations, the thickness of the shell region is substantially uniform.

In certain implementations, the intermediate region is movable relative to the shell region. The intermediate region may also be porous, with the bone interface forming a porous bone ingrowth surface. The bone interface is shaped to accommodate a standard resected bone geometry, and contours of the bone interface are different than an inner contour of the shell.

In certain embodiments, a method of manufacturing an orthopedic implant includes forming a shell region of the orthopedic implant and forming an intermediate region of the orthopedic implant, the intermediate region having different mechanical properties than the shell region. In certain implementations, the shell region and intermediate region are formed by rapid manufacturing, and the intermediate region may be formed of a different material or may have a different density or porosity than the shell region.

BRIEF DESCRIPTION OF THE DRAWINGS

The foregoing and other objects and advantages will be appreciated more fully from the following further description thereof, with reference to the accompanying drawings. These depicted embodiments are to be understood as illustrative and not as limiting in any way.

DETAILED DESCRIPTION

Figure 1:
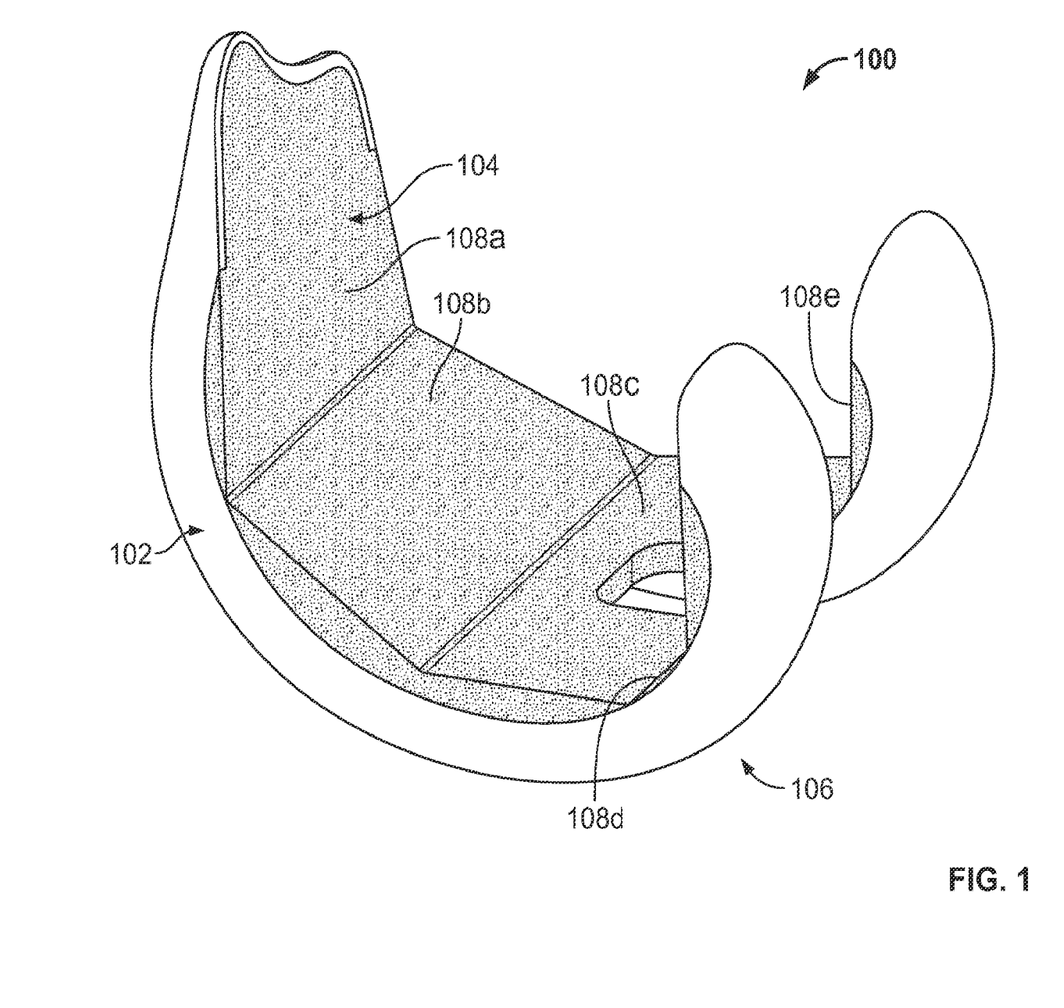
FIG. 1 shows a perspective view of an illustrative femoral implant.

To provide an overall understanding of the systems, devices and methods described herein, certain illustrative embodiments will now be described. For the purpose of clarity in illustration, the systems and methods will be described with respect to orthopedic knee implants. It will be understood by one of ordinary skill in the art that the systems, devices and methods described herein may be adapted and modified as is appropriate and that the systems, devices and methods described herein may be employed in other suitable applications, such as for other types of joints and orthopedic implants, and that other such additions and modifications will not depart from the scope hereof FIG. 1 shows a femoral component 100 of a knee replacement implant. In contrast to conventional implants that are made of a solid block of metal, the femoral component 100 is composed of two portions: a shell 102 and an intermediate portion 104. Together these two portions form a single implant component with an articulation surface 106 that contacts and articulates against a tibial implant component and a bone interface that contacts and affixes to a patient's femoral bone.

In particular, the shell 102 forms the outer portion of the femoral component 100 that interfaces with a tibial implant component. The outer articulation surface 106 is shaped to allow for natural movement of the femur during flexion and extension of the patient's femur and tibia after implantation. The inner portion of the shell 102 is designed to reduce the stress-shielding complications that can be caused by conventional knee replacements. In particular, the shell 102 has a degree of compliance and flexibility to allow for transmittal of forces incident on the femoral component 100 to the bone into which the femoral component is implanted, thus decreasing bone resorption and encouraging the maintenance of strong bone around the implant. The contours of the inner surface of the shell 102 are designed such that stress concentration points are reduced in order to more evenly spread the stresses and loads incident on the knee to the bone surrounding the implant. The shell 102, while being compliant to a degree, is also rigid and strong enough to maintain its integrity and keep the anatomical shape of the distal end of the femur under the wear and stresses caused by normal flexion and extension of the knee.

The intermediate portion 104 of the femoral component 100 forms an interface between the shell 102 and a patient's bone into which the femoral component 100 is implanted. The intermediate portion 104 may be integrally formed with the shell 102 or may be formed as a separate component that is bonded to an interior surface of the shell 102. In certain implementations, the intermediate portion 104 is a separate component that is bonded with the shell 102 in a manner that allows a small amount of relative movement between the intermediate portion 104 and the shell 102. For example, the intermediate portion 104 may be intermittently bonded to the shell 102 to allow for a small amount of flexing or movement between bonded areas. The intermediate portion 104 may also include channels or other cutout areas at an interface with the shell 102 that create small gaps, for example at areas of high bending, to allow the shell and intermediate portion to flex and move relative to each other.

In addition to the shapes of the shell 102 and intermediate portion 104 and the interface between the two portions of the component 100, the materials used for these two portions are selected to reduce stress shielding effects. In certain implementations, the materials used are selected such that the overall modulus of the femoral component 100 is near the modulus of the native bone into which the component is implanted. The shell 102 is made of a material that is able to maintain integrity under articulation forces while still transmitting those forces into the intermediate portion. For example, the shell 102 may be made of titanium, titanium alloy, stainless steel, cobalt-chromium, tantalum, zirconium alloy, other metallic alloys, or any other suitable material. The intermediate portion 104 is made of a material that does not significantly absorb forces transmitted through the shell and passes these forces on into the surrounding bone. The material also has strength to maintain its integrity and provide a solid interface with the bone. For example, the intermediate portion 104 may be made of polyethylene, polyetheretherketone (PEEK), polyurethane, porous metals such as tantalum, titanium, cobalt-chromium, stainless steel, starch, ceramic, hydroxyapatite, glass, or any other suitable material. A polymer intermediate portion may be made of polyetheretherketones (PEEK), also referred to as polyketones, poly-alpha-hydroxy acids, polycapropactones, polydioxanones, polyesters, polyglycolic acid, polyglycols, polylactides, polylactic acid, poly-D,L-lactic acid, poly-L, L-lactic acid, polyorthoesters, polyphosphates, polyphosphoesters, polyphosphonates, polysaccharides, polycaprolactone, polypropylene, fumarate, polytyrosine carbonates, or polyurethanes. In some instances, it may be desirable for the bone to biologically affix directly to the implant without the use of bone cement. In these cases, it may be desirable to form the intermediate portion from metal powder or wires that are bonded or sintered together to form a suitable ingrowth surface.

The materials selected for the shell 102 and intermediate portion 104 can provide an implant that has mechanical properties that are substantially similar to the properties of the native bone that the implant replaces. The native bone is made up of two types of bone, a dense outer cortical bone and a spongy inner cancellous bone. The materials used to make the shell 102 and intermediate portion 104 are selected to match the mechanical properties of the cortical bone and cancellous bone, respectively, to provide an implant that mimics the properties of the replaced bone more closely than a conventional implant. In addition to matching the mechanical properties, the materials used can also provides an implant that is lighter than a large metal conventional implant and can reduce a patient's discomfort, especially in the early stages following implantation surgery.

In some embodiments, the shell 102 and the intermediate portion 104 are manufactured as two separate components that are bonded together to form the femoral component 100. In some embodiments, the femoral component 100 is formed as one unitary component having two distinct regions forming the shell 102 and the intermediate portion 104. For example, rapid manufacturing processes can be used to form the femoral component 100 as a unitary component with distinct portions that have different properties and may be made of different materials. Rapid manufacturing machinery can create the distinct portions by changing the density of a material or type of material deposited to create the shell 102 and the intermediate portion 104. In some embodiments, a stronger material is deposited in the shell region, and a different, weaker material is deposited in the intermediate portion. In some embodiments, the same material is used but is deposited more densely in the shell region than in the intermediate portion. In either of these approaches, the shell 102 may be formed as a solid region while the intermediate portion 104 is formed as a weaker porous region that encourages bone ingrowth.

One or both of the shell 102 and intermediate portion 104 can also be formed with powdered metal by laser sintering or a similar process. Laser sintering can produce a shell or intermediate portion with multiple powdered metal materials or with powdered metal deposited at different densities in different areas of the implant. This approach allows for implant designs that are customized to provide varying local mechanical properties on a micro scale, for example by depositing higher modulus or denser materials in areas of a shell that experience higher stresses, while maintaining the macro-scale design and stress transmission properties of the implant.

The intermediate portion 104 includes a bone interface formed by faces 108a-e. As shown in FIG. 1, this bone interface is shaped to accommodate a standard shape of a patient's resected femoral bone following preparation of the bone using common techniques for knee replacement. In contrast to the shape of the prepared bone, the inner contours of the shell 102 are smooth and continuous, and thus the intermediate portion 104 serves as an intermediary that facilitates connection of the smooth contoured shell 102 to a patient's bone that is resected during surgery. The femoral component 100 may be cemented onto the patient's bone or may be implanted in a cementless procedure. In cementless implantations, the intermediate portion 104 is porous and forms an ingrowth surface that allows the surrounding bone to grow into the intermediate portion 104 to form a solid fixation of the femoral component 100 and surrounding bone.

In addition to providing desirable stress transmission properties, the shell 102 and intermediate portion 104 form an implant that creates a solid fixation between the faces 108a-e and a patient's bone during implantation. Because the modulus of the femoral component 100 is lower than a conventional solid implant, the component 100 is more compliant than the conventional solid implant. The compliance of the component 100 allows the implant to flex more easily when it is press-fit onto a patient's prepared bone. This flexibility allows for looser tolerances on the precision of bone cuts, as the implant can flex to accommodate a patient's bone without requiring a high press-fit force that may be required with a conventional implant. As a result of accommodating the bone and providing a better initial fit, the component 100 provides a strong permanent fixation between the bone and the component, for example by providing a "squeezing" pressure to the native bone that encourages ingrowth of the bone into the implant.

Figure 2:
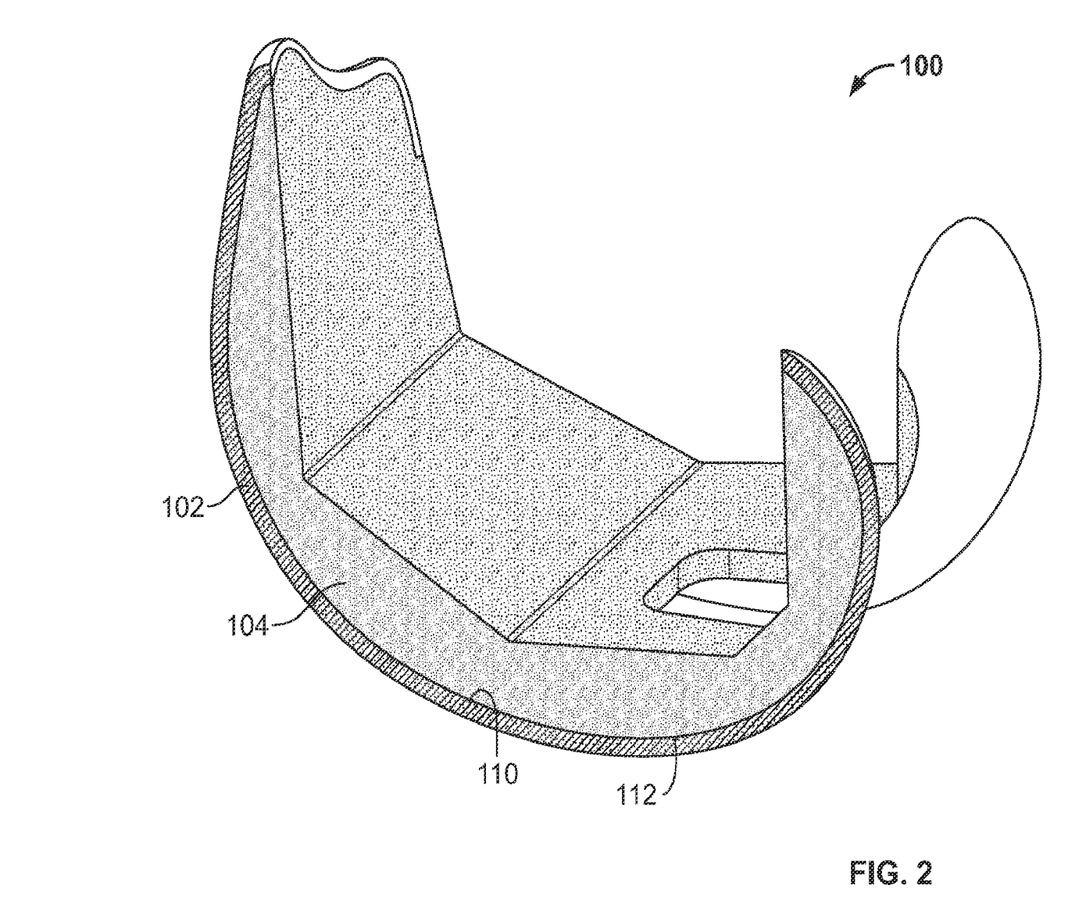
FIG. 2 shows a perspective view of a cross-section of the femoral implant shown in FIG. 1.

The two portions 102 and 104 of the femoral component 100 shown in FIG. 1 help reduce the effects of stress shielding and distribute loading forces and stresses over the femoral component 100. In particular, the shape and contours of the interior surface of the flexible shell 102 are designed to avoid sharp transitions and points where stress can be concentrated, leading to uneven distribution of incident forces over surrounding bone. The smooth, continuous contour of the shell 102 is shown in FIG. 2, which depicts a cross-section of the femoral component 100. The interior of the shell 102 and the intermediate portion 104 are shown, exposing the interface between the surface 110 of the intermediate portion 104 and the surface 112 of the shell 102. In certain implementations, the shell 102 and the intermediate portion 104 are integrally formed, for example by the use of rapid manufacturing techniques, and the interface between surface 110 and surface 112 is a transition from one type or design of material to another. In certain implementations, the shell 102 and the intermediate portion 104 are not integrally formed and are two separate components that are bonded together at the interface of these surfaces 110 and 112.

Figure 3:
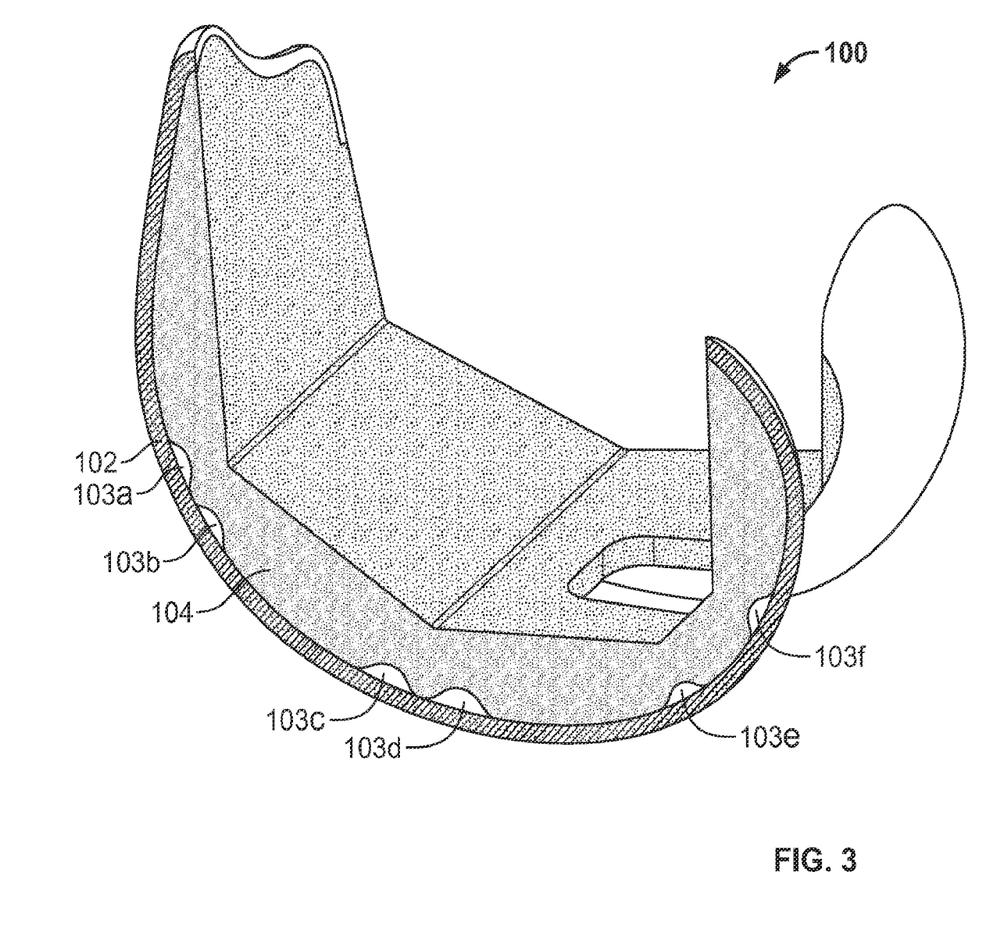
FIG. 3 shows a perspective view of an illustrative femoral implant having internal channels.

In some implementations, the interface between the shell 102 and the intermediate portion 104 allows for a small amount of relative movement between the two portions of the component 100. The relative movement can be accommodated by the inclusion of open channels at the interface of the shell 102 and the intermediate portion 104, as shown in FIG. 3. FIG. 3 depicts a cross-section of the component 100 that reveals optional internal channels 103a-f at the interface of the shell 102 and the intermediate portion 104. The channels 103a-f are disposed near the areas of the interior corners of the intermediate portion 104, but may be located at any suitable location along the interface between the shell 102 and the intermediate portion 104.

The channels 103a-f allow the component 100 to absorb relative movements between the shell and intermediate portion without interfering with bonding between the two components or creating significant wear particles that can compromise the implant. The intermediate portion 104 is able to flex slightly in the areas of the channels 103a-f without applying a force to or bending the shell 102 in the area of the flexing. Each of the channels 103a-f can be compressed by forces applied to the interior surface of the intermediate portion 104 until the channels are closed and the material of the intermediate portion 104 around the channels 103a-f contacts the shell 102. Because the channels 103a-f absorb this flexing of the intermediate portion 104 and shell 102, it may be preferable to locate the channels at areas of the interface between the shell and intermediate portion that experience the highest stresses or highest bending during normal use.

The surface 112 of the shell 102 contributes to the ability of the shell to spread loading stresses over bone surrounding the implant and to reduce concentration of these forces in one or more locations along the shell 102. The surface 112 is a smooth continuous surface that does not have sharp points or corners. The lack of sharp points and corners allows incident stresses to be spread over a wide area of the shell 102 rather than concentrating those forces at points or corners.

Figure 4A:
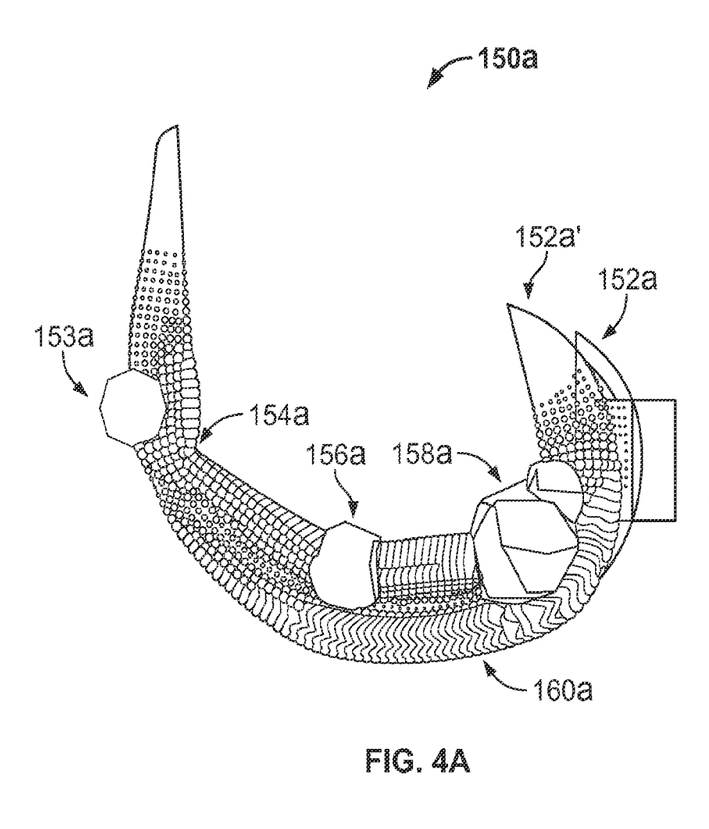
FIGS. 4A and 4B show a finite element analysis of two illustrative implant components.
Figure 4B:
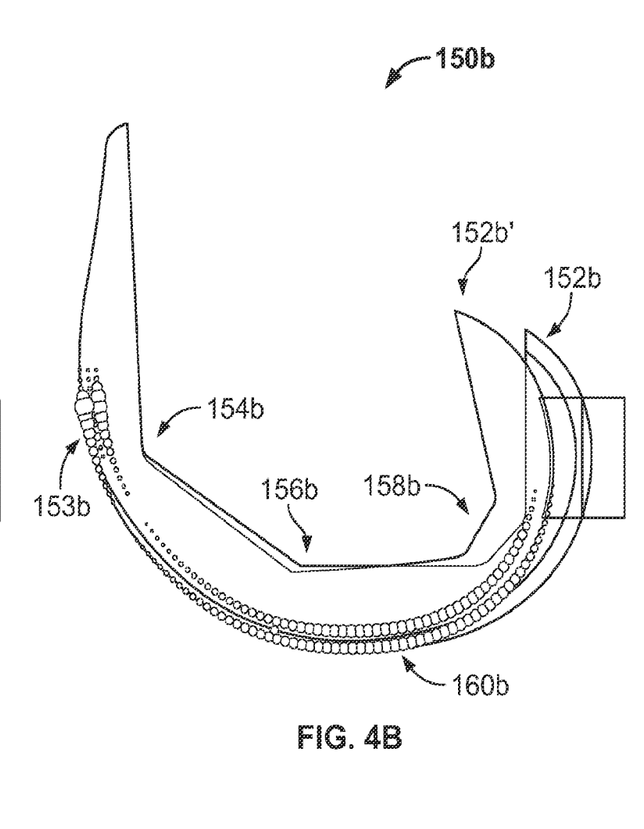

The stress distribution and transmission properties of the component 100 are described with respect to finite element analyses shown in FIGS. 4A and 4B. The analyses compare the properties of a conventional implant 150a, shown in FIG. 4A, made of cobalt chromium steel and a two-region implant 150b, shown in FIG. 4B, that is similar to component 100 and has a cobalt chromium shell and a polymeric intermediate portion, shown in FIG. 4B. A displacement of 5 mm was applied to both implants, displacing the posterior end of the solid steel implant 150a from initial position 152a to displaced position 152a' and displacing the posterior end of the two-region implant 150b from initial position 152b to displaced position 152b'. The spheres in FIGS. 4A and 4B indicate the internal stress created in the implants during displacement, and the size of the spheres is proportional to the magnitude of the stress. The solid implant 150a and two-region implant 150b were anchored at anterior points 153a and 153b, respectively, for the displacement, and the stress present at the outer surface in these areas is a result of the anchoring rather than an internal stress in the components generated during displacement.

The location and size of the stress spheres in FIGS. 4A and 4B highlight the different stress concentration and transmission properties of the two implants 150a and 150b. Implant 150a has a higher overall internal stress indicated by the number and larger sizes of the stress spheres in FIG. 4A. The internal stress is absorbed by the implant itself and would not be transmitted into surrounding bone during normal use, thereby causing the negative effects of stress shielding. Because of the rigid metal that makes up the implant 150a and the sharp corner transitions in the implant, the internal stress is not uniformly distributed, and the stress is focused at the corners 154a, 156a, and 158a. The concentrated forces are greater near the areas of greater displacement, as the stress increases from corner 154a to the posterior corners 156a and 158a. There is also a substantial amount of internal stress along the outer surface 160a of the implant 150a, shown by the stress spheres spread over the surface. The distribution of the stresses at the outer surface highlight the difference between the inner and outer contours, as the stresses are spread out over the outer surface 160a on the exterior side of the implant 150a but are concentrated at corners 154a, 156a, and 158a on the interior side.

Implant 150b exhibits a lower amount of internal stress than the implant 150a, as shown by the fewer spheres and smaller sphere sizes in FIG. 4B. Implant 150b also does not exhibit the stress concentration seen in implant 150a, as the internal corners 154b, 156b, and 158b on the polymeric intermediate portion do not have any appreciable concentrated stress in the deformed state. There is internal stress in the shell region of the implant 150b shown by the spheres on the outer surface 160b of the implant, but these spheres, and the stresses they represent, are lower than the outer stresses in implant 150a and are also substantially uniformly spread over the outer surface 160b. The substantially lower internal stress highlights the ability of the implant 150b to transmit forces into surrounding bone and reduce internal absorption of the forces, and thus reduce the negative effects of stress shielding that can be cause by a solid steel implant such as implant 150a.

Figure 5:
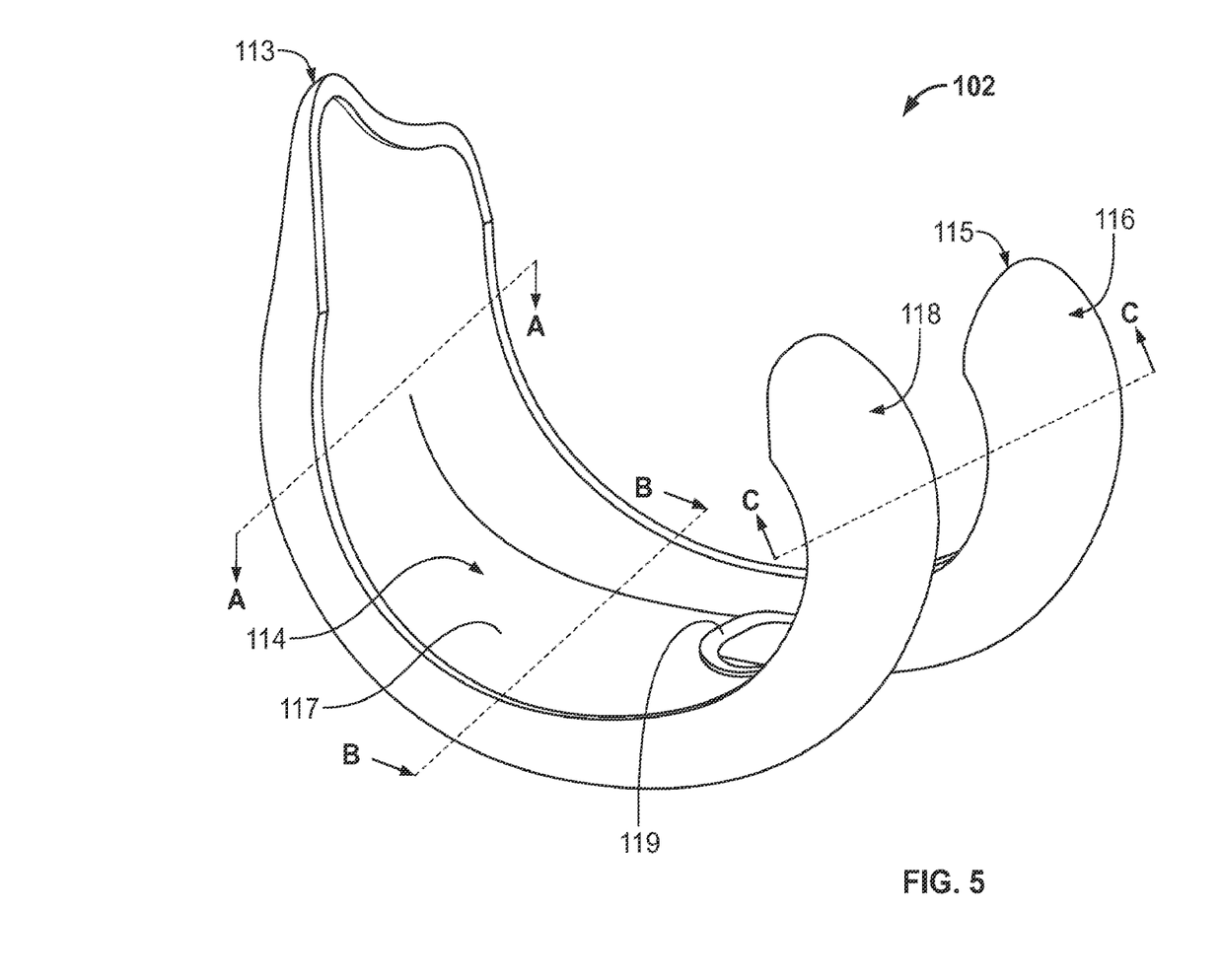
FIG. 5 shows a perspective view of a shell portion of the femoral implant shown in FIG. 1.

The stress transmission and distribution properties of the implant shown in FIG. 4B are created by the shape and design of the shell component, particularly the contours of the inner surface of the shell that interfaces with the intermediate portion, and the material used for both the shell and the intermediate portion. The shell 102 of implant component 100 is shown in FIG. 5 with the intermediate portion 104 removed from the component to expose the interior surface 114 of the shell 102. This configuration shows the substantially continuous and smooth contours of the interior surface 114. The interior surface 114 does not have sharp transitions and corners that can concentrate stresses during articulation of the shell 102, thereby allowing the knee implant shell 102 to evenly distribute the forces incident on the shell 102 during articulation. In particular, the interior surface 114 of the shell 102 exhibits smooth transitions between the posterior, inferior, and anterior sections of the shell 102, rather than sharp corners between these sections.

In addition to the continuous contours of the interior surface 114, the thickness of different areas of the shell 102 affects the distribution of stresses incident on the shell 102 and maintenance of the integrity of the shell material. The cross-sectional area of the shell can be configured to provide the desired stress distribution. In certain embodiments, the thickness of the shell 102 is maintained uniform throughout the shell from the posterior end 115 to the anterior end 113 to reduce uneven distribution of incident stresses. In certain implementations, the thickness of the shell 102 is varied from the anterior end 113 to the posterior end 115 to maintain a uniform cross-sectional area of different locations along the shell 102, helping to maintain strength and rigidity of the shell.

Figure 6A:
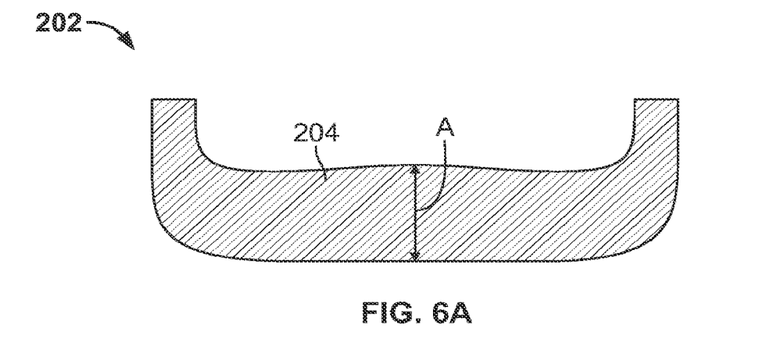
FIGS. 6A-C show cross-section views of an illustrative femoral implant shell having a substantially uniform cross-sectional area.
Figure 6B:
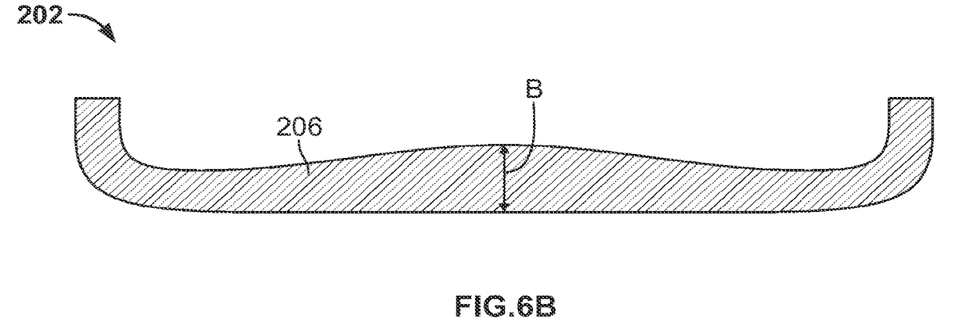
Figure 6C:
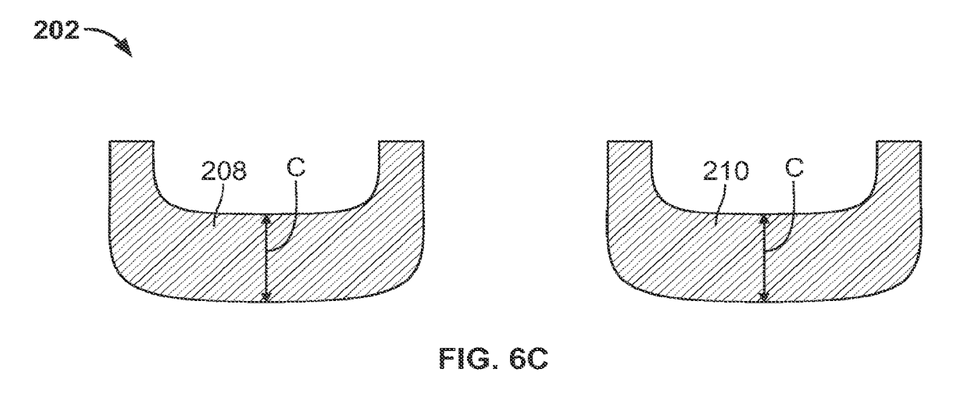

Certain embodiments of shells having substantially uniform cross-sectional area or substantially uniform thickness are illustrated by viewing the cross-sectional profile of a femoral implant component shell at different locations along the shell, such as at the locations indicated by lines A-A, B-B, and C-C shown in FIG. 5. FIGS. 6A-C illustrate one approach in which the cross-sectional area of a shell 202 is maintained substantially uniform by varying the thickness of the shell. The substantially uniform cross-sectional area of the shell 202 contributes to the ability of the shell to maintain its shape and material integrity, as it affects the second moment of inertia resistance of the shell, which is the resistance to bending under forces applied to the shell. Specifically, maintaining a substantially uniform cross-sectional area in a shell can help create substantially the same resistance to bending under force at different areas of the shell that have different external geometries, such as different widths. The uniform cross-sectional area and resistance thus provides a shell that does not have points that are significantly more compliant and susceptible to unwanted bending than other points within the shell. In addition to the cross-sectional area, the thickness of the shell can be varied to maintain uniformity for another suitable mechanical property, such as moment of inertia and section modulus.

To maintain a uniform cross-sectional area, the thickness of an implant shell can be varied throughout the implant, and wider areas of the component are thinner than narrower areas of the component. FIG. 6A shows a cross-sectional profile taken at a location on the shell 202 that corresponds to the line A-A of shell 102 in FIG. 5. The cross-sectional profile has a face 204 that includes the thickness "A" of the shell 202 at this location. The area of the face 204 is substantially uniform compared to cross-sections taken at other areas of the shell 202.

FIG. 6B shows a cross-sectional profile of the shell 202 taken at a second location that corresponds to the line B-B of shell 102 in FIG. 5. The cross-sectional profile includes a face 206 having a thickness "B" of the shell 202 at this location. Because the shell 202 is wider at this location, the thickness B is smaller than the thickness A shown on face 204 in FIG. 6A. The smaller thickness at this location maintains the substantially uniform area of the face 206 and the face 204.

FIG. 6C shows a third cross-sectional profile of the shell 202 taken at a location of the shell 202 that corresponds to the line C-C of shell 102 in FIG. 5. The cross-sectional profile shown includes two faces, face 208 on a condylar portion corresponding to condylar portion 116 of shell 102 and face 210 on a condylar portion corresponding to condylar portion 118 of shell 102. The two faces 208 and 210 have the same thickness "C", which is greater than both of the thicknesses A and B shown on faces 204 and 206, respectively. The thickness C is selected such that the sum of the areas of the faces 208 and 210 is substantially equal to the cross-sectional area of face 206 and the area of face 204.

In certain implementations, it may be preferable to maintain a uniform thickness throughout an implant shell rather than a uniform cross-sectional area. Because the width and other dimensions of the shell differ, a uniform thickness creates a varied cross-sectional area and, potentially, a varied resistance to bending forces. Some implant materials, however, are strong enough that there is not a significant resistance to bending forces with minor changes in cross-sectional area, and thus a uniform thickness does not result in a significant bending risk. The uniform thickness may be preferable for such an implant to maintain uniform transmission of forces incident on the implant into surrounding bone structure. Forces on the implant are absorbed to some degree by the implant material, and thicker areas of an implant may absorb more force than thinner areas due to the increased material in the thicker areas. Maintaining a uniform thickness of an implant keeps the absorbed forces substantially the same throughout an implant shell, and preferably low enough to transmit most of the normal functioning forces into surrounding bone to maintain its integrity.

Figure 7A:
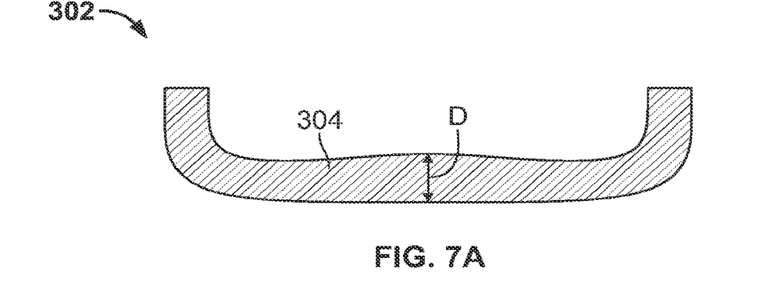
FIGS. 7A-C show cross-section views of an illustrative femoral implant shell having a substantially uniform thickness.
Figure 7B:
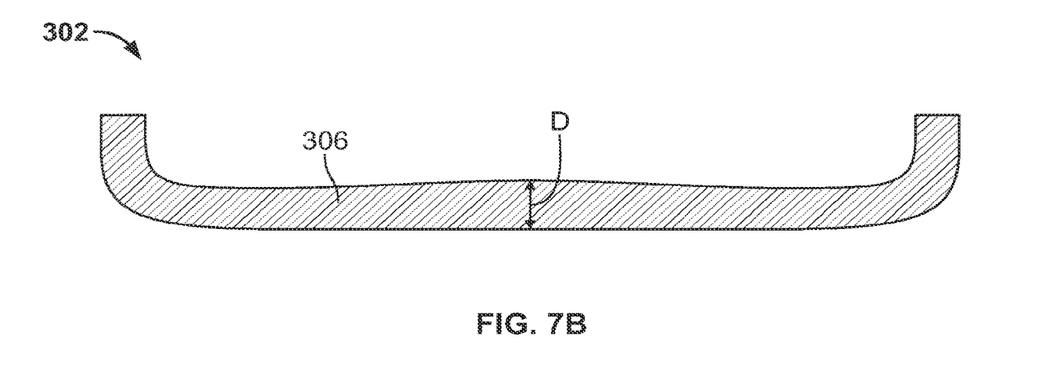
Figure 7C:
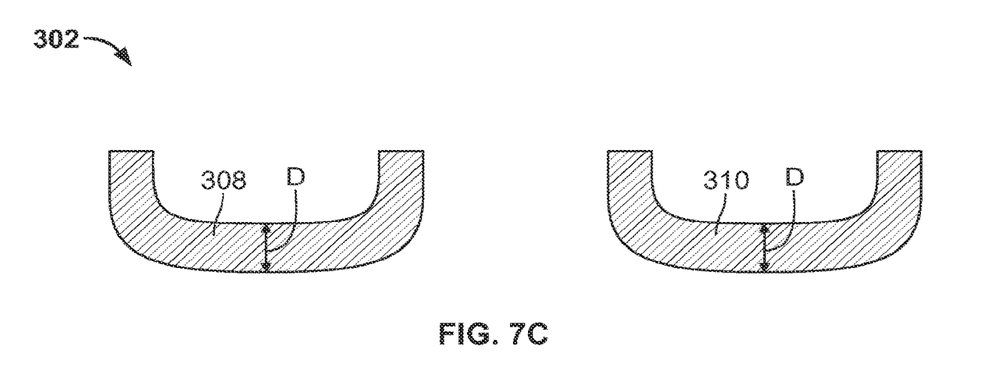

FIGS. 7A-C illustrate this approach in shell 302, which has a substantially uniform thickness. FIG. 7A shows a cross-sectional profile of a shell 302 taken at a location corresponding to the line A-A shown in FIG. 5. The cross-sectional area includes a face 304 having a thickness "D", and this thickness is substantially constant throughout the shell.

FIG. 7B shows a second cross-sectional profile of shell 302 taken at a location on the shell corresponding to the line B-B and shown in FIG. 5. The cross-sectional profile includes a face 306 and the same thickness D as face 304 shown in FIG. 7A. In this implementation, while the thickness of the implant is uniform, the cross-sectional is not uniform, as the face 306 has an area larger than the face 304. However, the uniform thickness keeps the absorbance of incident forces substantially constant, as there is no significant difference in the amount of shell material between the external surface 312 and the internal surface 314 along either cross-sectional face 304 or 306.

FIG. 7C shows a third cross-sectional profile of the shell 302 taken at a location corresponding to the location shown by line C-C in FIG. 5. Again, the cross-sectional profile shows the thickness D on the faces 308 and 310 of condylar portions of the shell 302. Each of these faces 308 and 310 has an area that is different from the areas of faces 304 and 306, but the uniform thickness again allows for transmittal of forces through the faces 308 and 310 similar to the faces 304 and 306.

The illustrated approaches of maintaining either a uniform cross-sectional area or uniform thickness of an implant shell help reduce stress risers and provide uniform transmission of incident stresses over an area of bone. Depending on the type of implant, material, or incident forces in a particular application, both the cross-sectional area and thickness may be designed to accommodate specific needs for the implant. The designs face a trade-off between providing a thick implant shell that resists bending and a thin implant shell that reduces absorbance of incident forces. In certain implementations, the requirements for a particular implant are met by varying both the cross-sectional area and thickness slightly throughout an implant shell to provide adequate bending resistance and uniform force transmission in different areas of the shell.

The external stresses which are incident on an implant shell, such as shell 102, during articulation of a knee may not be uniformly distributed over the external surface of the shell due to the anatomic motion of the knee. For example, the anterior area 117, the condylar portions 116 and 118, and the junction 119 between the two condylar portions of shell 102 shown in FIG. 5 may experience higher stresses at various points during articulation of the shell. In order to maintain the integrity and shape of the shell 102 under these increased forces while still maintaining the substantially uniform cross-sectional area or thickness of the shell 102, it may be desirable in certain implementations to provide reinforcement to these areas that experience higher stresses.

Figure 8:
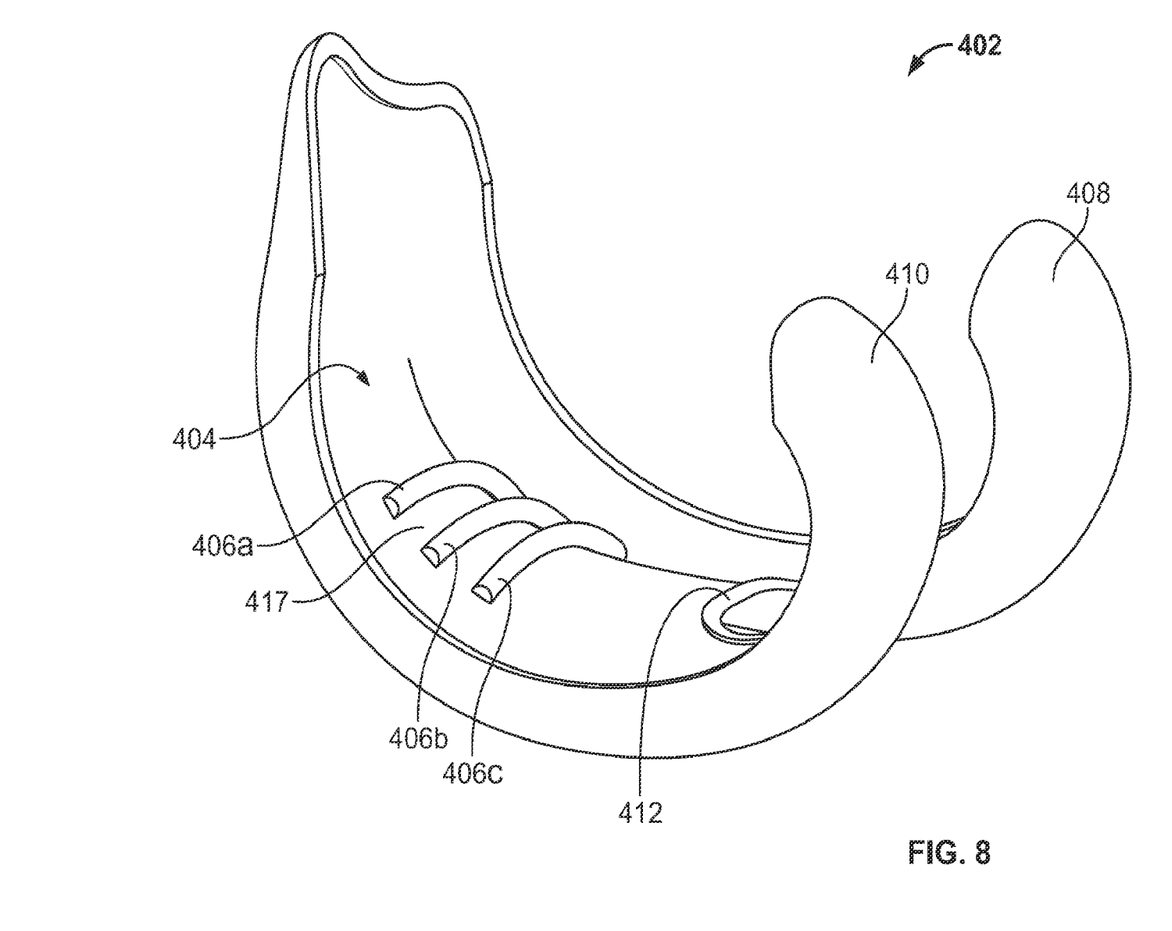
FIG. 8 shows a perspective view of an illustrative femoral implant shell having anterior reinforcing ribs.

FIG. 8 shows a shell 402 that includes reinforcements in areas of higher stress caused by non-uniform normal stresses incident on the shell. The shell 402 has an interior surface 404 that is substantially continuous and smooth, as discussed above with respect to the inner surface 114 of the shell 102. The interior surface 404 has an anterior portion 417 on which heightened stress is incident during normal articulation of the shell 402. The heightened stress may be present at anterior portion 417 as a result of normal motion of the knee, for example from contact forces when a patient's foot strikes the ground while walking. To address this heightened stress, the anterior portion 417 has reinforcing ribs 406a-c to provide added support to this portion of the interior surface 404. These reinforcements allow the shell 402 to articulate under non-uniform forces without bending or deforming in the area of anterior portion 417.

The reinforcing ribs 406a-c are shown in FIG. 8 extending along the interior surface 404 of the shell 402. In such an implementation, an intermediate portion, which may be substantially similar to the intermediate portion 104 shown in FIG. 1, is bonded to the shell 402 and has a shell interface surface that accommodates the reinforcing ribs 406a-c to maintain close contact with the interior surface 404. Because the ribs cover only the anterior portion 417, the substantially smooth and continuous contour of the shell 402 is mostly maintained over the full surface 404. The reinforcing ribs 406a-c may be designed with curved edges to avoid introducing sharp transitions that could potentially act as stress concentration points. In certain implementations, the reinforcing ribs are disposed in an internal portion of the shell 402, for example by depositing the material of shell 402 more densely in the interior, or by using a stronger material for interior portions, without introducing any change to the smooth interior surface 404.

In addition to the ribs 406a-c, the shell 402 may contain additional reinforcements to provide added support at the posterior condylar portions 408 and 410 and the junction 412 between the two condylar portions. The additional support at condylar portions may be desired due to the decreased width and material mass of the shell 402 in those areas. Instead of providing an implant shell having thicker material throughout these portions, the reinforcing ribs may be desirable to provide the added support without significantly affecting the transmission of forces into bone.

Figure 9:
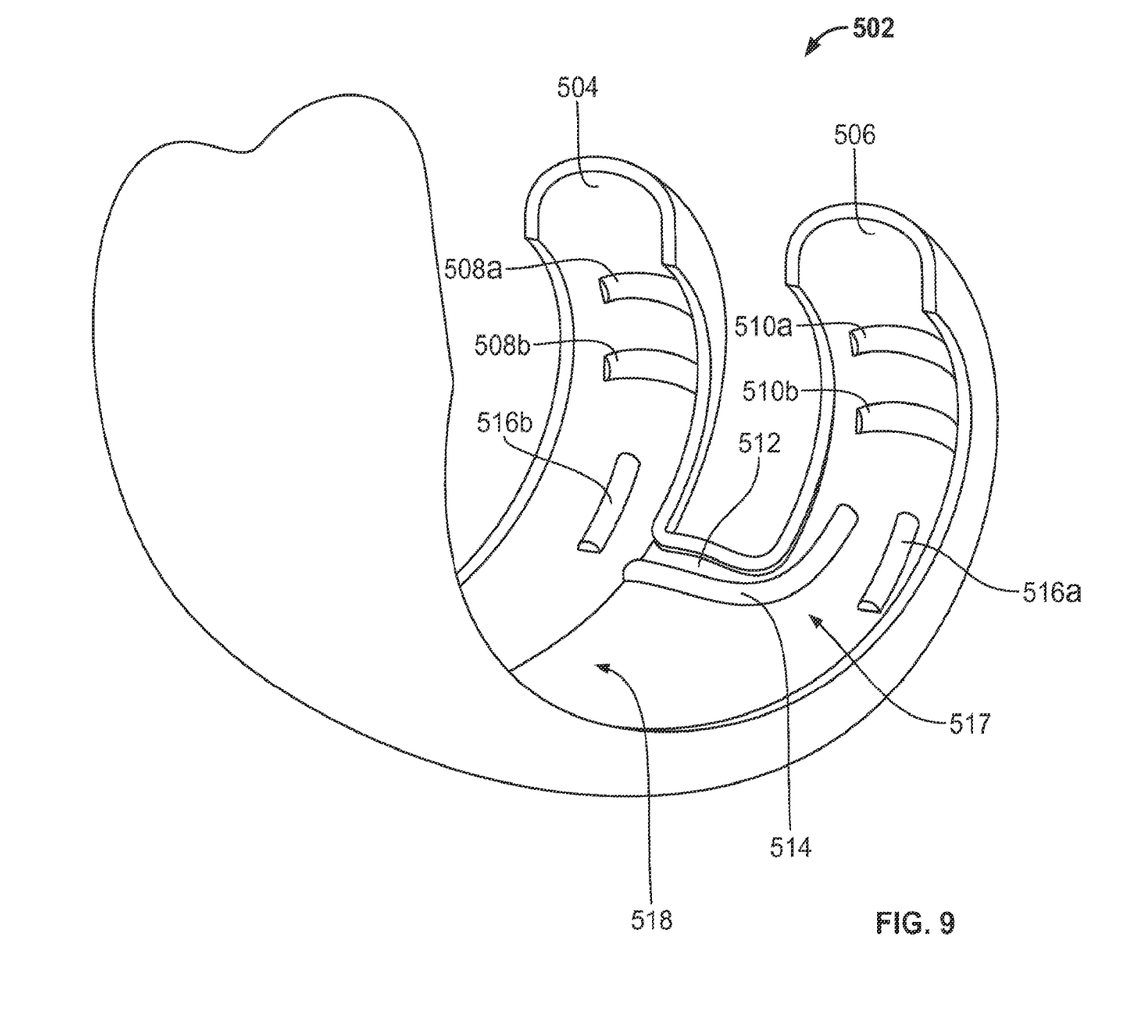
FIG. 9 shows a perspective view of an illustrative femoral implant shell having condylar reinforcing ribs.

FIG. 9 shows a perspective view of a shell 502 having a series of reinforcements on a posterior portion 517 of the shell. The reinforcements include condylar ribs 508a-b and 510a-b, side ribs 516a-b and a junction rib 514. The condylar ribs 508a-b on condylar portion 504 and the condylar ribs 510a-b on the condylar portion 506 give added support to these condylar portions to resist deformation or twisting of the condylar portions as a knee approaches full flexion. The longitudinal ribs 516a-b resist bending and deformation of the posterior portion 517 of the shell 502 during flexion of the implant. The junction rib 514 complements this support and provides additional reinforcement at the junction 512 between the condylar portions 504 and 506 to resist twisting or deformation of one of the condylar portions 504 and 506 relative to the other.

It is to be understood that the foregoing description is merely illustrative and is not to be limited to the details given herein. While several embodiments have been provided in the present disclosure, it should be understood that the disclosed systems, devices, and methods, and their components, may be embodied in many other specific forms without departing from the scope of the disclosure.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

The invention claimed is:

1. A femoral component of a knee implant, the femoral component comprising:
 a shell region having an anterior end, a posterior end, a lateral end, a medial end, an outer joint articulation surface, an interior surface, and a plurality of strengthening ribs formed directly on the interior surface of the shell region, the interior surface otherwise comprising a smooth surface; and
 an intermediate region located adjacent to the interior surface of the shell region, the intermediate region comprising:
  a bone interface surface, the bone interface surface includes a plurality of planar portions shaped to accommodate a patient's resected femoral bone, and
  a shell interface surface configured to interface the shell region, the shell interface surface configured to accommodate the plurality of strengthening ribs to maintain close contact between the intermediate region and the interior surface of the shell region;
 wherein the interior surface of the shell region is a smooth continuous surface arranged and configured to allow stress distribution over a wide area of the shell region;
 wherein the intermediate region exhibits a different modulus of elasticity than the shell region;
 wherein the plurality of strengthening ribs extend laterally between the lateral end and the medial end, at least one of the plurality of strengthening ribs disposed within a medial condylar region of the shell region, at least one of the plurality of strengthening ribs disposed within a lateral condylar region of the shell region, and at least one of the plurality of strengthening ribs disposed at a junction of the lateral and medial condylar regions, the strengthening rib at the junction extending laterally between the lateral and medial ends before curving anterior-posteriorly along a portion of the medial and lateral condyles.

2. The femoral component of claim 1, wherein the plurality of planar portions are separated from each other via an angle or corner.

3. The femoral component of claim 1, wherein the interior surface of the shell region includes smooth transitions between a posterior section of the shell region, an inferior section of the shell region, and an anterior section of the shell region.

4. The femoral component of claim 1, wherein the cross-sectional area of the shell region includes a uniform cross-sectional area.

5. The femoral component of claim 4, wherein:
 the shell region has a plurality of cross-sections taken perpendicular to the outer joint articulation surface; and
 each of the plurality of cross-sections includes a corresponding cross-sectional profile of the shell region and a corresponding cross-sectional area of the shell region, the cross-sectional profiles of the shell region being varied amongst the plurality of cross-sections, the plurality of cross-sectional areas of the shell region being uniform amongst the plurality of cross-sections.

6. The femoral component of claim 5, wherein the shell region includes a thickness and a width, the thickness of the shell region being varied from an anterior portion to a posterior portion and the width of the shell region being varied from the anterior portion to the posterior portion, the thickness and the width being inversely varied relative to each other.

7. The femoral component of claim 1, wherein the intermediate region has at least one of a different density than the shell region or a different porosity than the shell region.

8. The femoral component of claim 1, wherein the intermediate region is comprised of a different material than the shell region.

9. The femoral component of claim 1, wherein at least one of the plurality of strengthening ribs is disposed at an anterior portion of the shell region.

10. The femoral component of claim 1, wherein at least one of the plurality of strengthening ribs is disposed in an internal portion of the interior surface of the shell region.

11. The femoral component of claim 1, wherein the plurality of strengthening ribs include curved edges to avoid sharp transitions.

12. The femoral component of claim 1, wherein the intermediate region comprises at least one channel at an interface with the shell region, the channel configured to provide a gap to allow relative movement between the shell region and the intermediate region.

13. The femoral component of claim 10, wherein the internal portion of the shell region is separate from an edge of the shell region.

14. The femoral component of claim 1, wherein the plurality of strengthening ribs are disposed in an internal portion of the interior surface of the shell region via depositing a material of the shell region more densely in the internal portion.

15. An orthopedic femoral component of a knee implant comprising:
 a shell region having an anterior end, a posterior end, a lateral end, a medial end, an outer joint articulation surface and an interior surface, the interior surface of the shell region comprising a smooth and continuous surface arranged and configured to reduce stress shielding and to provide improved stress distribution over the implant, the shell region further comprising a plurality of strengthening ribs formed directly on the interior surface of the shell region, the plurality of strengthening ribs extending from the smooth interior surface, the plurality of strengthening ribs extend laterally between the lateral end and the medial end, at least one of the plurality of strengthening ribs disposed within a medial condylar region of the shell region and at least one of the plurality of strengthening ribs disposed within a lateral condylar region of the shell region; and an intermediate region located adjacent to the interior surface of the shell region, the intermediate region comprising:
  a bone interface surface, the bone interface surface includes a plurality of faces shaped to accommodate a patient's resected femoral bone, and
  a shell interface surface configured to interface the shell region, the shell interface surface configured to accommodate the plurality of strengthening ribs to maintain close contact between the intermediate region and the interior surface of the shell region;
wherein the intermediate region exhibits a different modulus of elasticity than the shell region.

16. The orthopedic implant of claim 15, wherein the intermediate region is integrally formed with the shell region.

17. The orthopedic implant of claim 15, wherein the intermediate region is separately formed and bonded to the interior surface of the shell region.

18. The orthopedic implant of claim 15, wherein the intermediate region is movable relative to the shell region.

19. The orthopedic implant of claim 15, wherein the intermediate region comprises at least one channel at an interface with the shell region, the channel configured to provide a gap to allow relative movement between the shell region and the intermediate region.

20. The orthopedic implant of claim 15, wherein at least one of the plurality of strengthening ribs is disposed in an internal portion of the interior surface of the shell region, and
  wherein the internal portion of the shell region is separate from an edge of the shell region.

* * * * *